United States Patent [19]

Froyd

[11] 4,156,722

[45] May 29, 1979

[54] DINITROANILINES FOR CONTROL OF SOIL-BORNE PHYTOPATHOGENS

[75] Inventor: James D. Froyd, Fountaintown, Ind.

[73] Assignee: Eli Lilly and Company, Indianapolis, Ind.

[21] Appl. No.: 841,874

[22] Filed: Oct. 13, 1977

Related U.S. Application Data

[62] Division of Ser. No. 668,359, Mar. 19, 1976, Pat. No. 4,065,559.

[51] Int. Cl.$^2$ ............................................. A01N 9/16
[52] U.S. Cl. .................................... 424/228; 424/330
[58] Field of Search ............... 424/304, 309, 317, 324, 424/330, 228

[56] References Cited

U.S. PATENT DOCUMENTS

| | | | |
|---|---|---|---|
| 3,119,736 | 1/1964 | Clark et al. | 424/330 |
| 4,045,466 | 8/1977 | Beck et al. | 424/304 |

OTHER PUBLICATIONS

Chemical Abstracts, vol. 73 (1970), p. 13451e.

*Primary Examiner*—V. D. Turner
*Attorney, Agent, or Firm*—Kathleen R. S. Page; Everet F. Smith

[57] ABSTRACT

A class of 2,6-dinitroanilines having a broad range of substituent groups on the anilino nitrogen and in the 3- and 4-positions of the phenyl ring are used for the protection of plants against soil-borne phytopathogens of the genus Phytophthora.

11 Claims, No Drawings

DINITROANILINES FOR CONTROL OF SOIL-BORNE PHYTOPATHOGENS

This is a division, of application Ser. No. 668,359, filed Mar. 19, 1976, and issued Dec. 27, 1977 as U.S. Pat. No. 4,065,559.

BACKGROUND OF THE INVENTION

This invention relates to the control of phytopathogens which attack plants through the soil. More particularly, the invention provides a new method of protecting plants from soil-borne phytophthora phytopathogens.

Beginning in the early 1960's, Soper disclosed that 2,6-dinitroanilines possess herbicidal activity, most notably preemergent herbicidal activity. See, for example, U.S. Pat. Nos. 3,111,403; 3,257,190; 3,332,769; and 3,367,949. Following Soper's lead, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Pat. No. 787,939.

Malichenko et al., *Fiziol. Aktiv. Veschestva* 1969, 2, 75–8; C.A. 73, 13451e (1970), disclose that some 2,6-dinitroanilines bearing a trifluoromethyl group in the 4-position possess some activity against *Phytophthora infestans*, the causative organism of late blight of tomatoes.

Clark et al., U.S. Pat. No. 3,119,736, disclose a broad class of compounds alleged to be fungicides. The generic description of such compounds includes dinitroanilines, but there is no specific disclosure of 2,6-dinitroanilines.

Zsolnai, *Biochemical Pharmacology* 5, 287–304 (1961), discloses that certain 2,4-dinitroanilines possess some fungicidal activity against various organisms. No 2,6-dinitroaniline was disclosed.

Buczacki, *Ann. Appl. Biol.* 75, 25 (1973), tested five dinitroanilines against clubroot of cabbage with variable results. He concluded, however, that "dinitroanilines are unlikely to be of value in the control of clubroot."

Eshel and Katan, *Weed Science* 20, 243 (1972), observed the effects of four dinitroanilines against *Rhizoctonia solani* and *Fusarium oxysporum*. Three of the four test compounds decreased the growth of *R. solani* at the highest rates tested, but none of the four appreciably decreased the growth of *F. oxysporum* at any rate tested.

A study of trifluralin-treated soil by Breazeale and Camper, *Appl. Microbiol.* 19, 379 (1970), indicated that the actinomycete population increased as compared to the control, while population of bacteria and fungi decreased.

SUMMARY OF THE INVENTION

The present invention provides a method for reducing the vigor of soil-borne phytophthora phytopathogens which comprises applying to soil infested with the phytopathogens a fungicidally-effective amount of a 2,6-dinitroaniline of one of the following formulae:

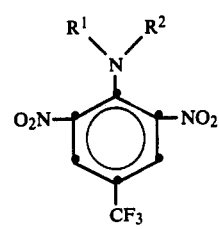

wherein
$R^1$ is H, $C_2$–$C_3$ alkyl, chloroethyl, cyanoethyl, $C_3$–$C_4$ alkenyl or halo $C_3$–$C_4$ alkenyl;
when $R^1$ is H,
$R^2$ is $N(R^3)_2$, normal $C_3$–$C_6$ alkyl, branched $C_4$–$C_7$ alkyl containing no tertiary carbon atoms, 1-hydroxy-2-propyl, methallyl, N-ethyl-3-piperidyl, 2,6-dimethyl-1-piperidyl, 2,5-dimethylpyrrolidino or 2-ethyl-1-piperidyl;
When $R^1$ is not H,
$R^2$ is 3-chloro-n-butyl, $C_3$–$C_4$ alkenyl, halo $C_3$–$C_4$ alkenyl, chloroethyl, cyclopropylmethyl, cyanoethyl, hydroxyethyl, n-$C_3H_7$, or epoxypropyl;
each $R^3$ is independently $C_1$–$C_3$ alkyl;

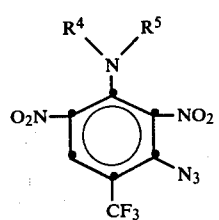

wherein
$R^4$ is H or $C_1$–$C_3$ alkyl;
when $R^4$ is H,
$R^5$ is $N(R^6)_2$, $C_1$–$C_7$ normal or branched alkyl containing no tertiary carbon atoms, $C_3$–$C_4$ alkenyl or N-methyl-2-propionamido;
when $R^4$ is $C_1$–$C_3$ alkyl,
$R^5$ is $C_1$–$C_4$ alkyl or $C_3$–$C_4$ alkenyl;
and each $R^6$ is independently $C_1$–$C_3$ alkyl;

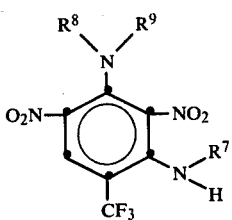

wherein
$R^7$ is H, CN, $C_1$–$C_3$ alkyl or $C_2$–$C_3$ alkanoyl;
$R^8$ is H or $C_1$–$C_3$ alkyl;
when $R^8$ is H,
$R^9$ is $N(R^{10})_2$, $C_1$–$C_6$ normal or branched alkyl containing no tertiary carbon atoms, or $C_3$–$C_4$ alkenyl;
when $R^8$ is $C_1$–$C_3$ alkyl,
$R^9$ is $C_1$–$C_4$ $C_3$ alkyl, halo $C_3$–$C_4$ alkenyl, propargyl, tetrahydrofurfuryl or $C_3$–$C_4$ alkenyl; and
each $R^{10}$ is independently $C_1$–$C_3$ alkyl;

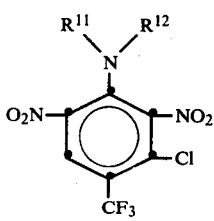

(IV)

wherein
R$^{11}$ is H or C$_1$–C$_3$ alkyl;
when R$^{11}$ is H,
R$^{12}$ is N(R$^{13}$)$_2$, C$_1$–C$_4$ normal or branched alkyl containing no tertiary carbon atoms, or C$_3$–C$_4$ alkenyl;
when R$^{11}$ is C$_1$–C$_3$ alkyl,
R$^{12}$ is C$_1$–C$_3$ alkyl or C$_3$–C$_4$ alkenyl;
and each R$^{13}$ is independently C$_1$–C$_3$ alkyl;

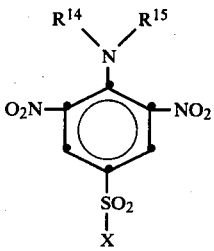

(V)

wherein
X is N(R$^{16}$)$_2$, chloro, CH$_3$, N=S(R$^{17}$)$_2$, N(R$^{18}$)CH$_2$Het, C$_1$–C$_2$ alkoxy, N=CHN(CH$_3$)$_2$, N=C(R$^{19}$)OR$^{20}$, N=CHOR$^{21}$ or N$_3$;
R$^{14}$ is H, C$_3$–C$_4$ alkenyl or C$_1$–C$_4$ alkyl;
when R$^{14}$ is H,
R$^{15}$ is C$_3$–C$_7$ secondary alkyl;
when R$^{14}$ is not H,
R$^{15}$ is C$_1$–C$_5$ alkyl, cyclopropylmethyl, C$_5$–C$_6$ cycloalkyl, C$_3$–C$_4$ alkenyl, halo C$_2$–C$_3$ alkyl or halo C$_3$–C$_4$ alkenyl;
one of R$^{16}$ is H or CH$_3$ and the other is H, SCCl$_3$, CH$_3$, phenylthio, OH, C$_1$–C$_4$ alkoxy or NH$_2$;
each R$^{17}$ is independently C$_1$–C$_2$ alkyl, phenyl or benzyl;
Het is 2,5-dimethylpyrrolidino, piperidino, morpholino, C$_1$–C$_2$ alkylpiperidino, hexahydroazepino, 2,2-dimethylaziridino, or C$_1$–C$_2$ alkylpiperazino;
R$^{18}$ is H or methyl;
R$^{19}$ is C$_1$–C$_2$ alkyl or phenyl;
R$^{20}$ is C$_1$–C$_4$ alkyl; and
R$^{21}$ is C$_1$–C$_2$ alkyl;

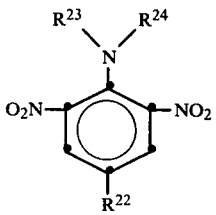

(VI)

wherein
R$^{22}$ is cyano C$_1$–C$_3$ alkyl, halo, or C$_1$–C$_4$ alkyl;
R$^{23}$ is H, chloroethyl, hydroxyethyl or C$_1$–C$_4$ nontertiary alkyl; and
when R$^{23}$ is H,
R$^{24}$ is C$_3$–C$_7$ secondary alkyl;

when R$^{23}$ is not H,
R$^{24}$ is C$_1$–C$_4$ nontertiary alkyl, chloroethyl, hydroxyethyl, halo C$_3$–C$_4$ alkenyl or C$_3$–C$_4$ alkenyl;

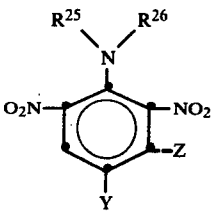

(VII)

wherein
Y is H or CH$_3$;
Z is NH$_2$, Cl, CH$_3$, or OCH$_3$;
R$^{25}$ is H or C$_2$–C$_4$ nontertiary alkyl; and
when R$^{25}$ is H,
R$^{26}$ is C$_3$–C$_7$ secondary alkyl or N-methyl-2-propionamido;
when R$^{25}$ is C$_2$–C$_4$ nontertiary alkyl,
R$^{26}$ is C$_2$–C$_4$ nontertiary alkyl or C$_3$–C$_4$ alkenyl;

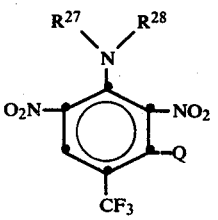

(VIII)

wherein
Q is OH, OCH$_3$, SCH$_3$, SCN, SCH$_2$CH$_2$CN, SCH$_2$CN, SCH$_2$CO$_2$CH$_3$, CO$_2$H, CONH$_2$, or CN;
R$^{27}$ is H or C$_1$–C$_3$ alkyl; and
when R$^{27}$ is H,
R$^{28}$ is N(CH$_3$)$_2$ or C$_1$–C$_6$ normal or branched alkyl containing no tertiary carbon atoms; and
when R$^{27}$ is C$_1$–C$_3$ alkyl,
R$^{28}$ is propargyl, tetrahydrofurfuryl or C$_1$–C$_4$ nontertiary alkyl.

A particularly preferred embodiment is the method as described above wherein the dinitroaniline is a compound of the formula

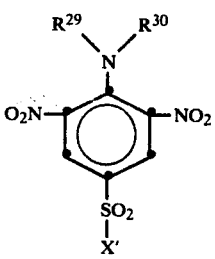

wherein
X' is N(R$^{31}$)$_2$, chloro, CH$_3$, N=S(R$^{32}$)$_2$, N(R$^{33}$)CH$_2$Het', C$_1$–C$_2$ alkoxy, N=CHN(CH$_3$)$_2$, N=C(R$^{34}$)OR$^{35}$, N=CHOR$^{36}$ or N$_3$;
R$^{29}$ is H, C$_3$–C$_4$ alkenyl or C$_1$–C$_4$ alkyl;
when R$^{29}$ is H,
R$^{30}$ is C$_3$–C$_7$ secondary alkyl;
when R$^{29}$ is not H,
R$^{30}$ is C$_1$–C$_5$ alkyl, cyclopropylmethyl, C$_5$–C$_6$ cycloalkyl, C$_3$–C$_4$ alkenyl, halo C$_2$–C$_3$ alkyl or halo C$_3$–C$_4$ alkenyl;

one of $R^{31}$ is H or $CH_3$ and the other is H, $SCCl_3$, $CH_3$, phenylthio, OH, $C_1$–$C_4$ alkoxy or $NH_2$;

each $R^{32}$ is independently $C_1$–$C_2$ alkyl, phenyl or benzyl;

Het' is 2,5-dimethylpyrrolidino, piperidino, morpholino, $C_1$–$C_2$ alkylpiperidino, hexahydroazepino, 2,2-dimethylaziridino, or $C_1$–$C_2$ alkylpiperazino;

$R^{33}$ is H or methyl;

$R^{34}$ is $C_1$–$C_2$ alkyl or phenyl;

$R^{35}$ is $C_1$–$C_4$ alkyl; and $R^{36}$ is $C_1$–$C_2$ alkyl.

It will be noted that the above formula is equivalent to Formula V above.

DESCRIPTION OF THE PREFERRED EMBODIMENT

For the most part, the compounds used in the method of this invention are well known in the agricultural chemical art. In order to assure that the reader fully understands the invention, however, the following compounds exemplary of those used in the invention are mentioned. It will be understood that these compounds are by no means exhaustive of the invention, nor do they bound its scope. They are, however, typical examples of the compounds useful herein.

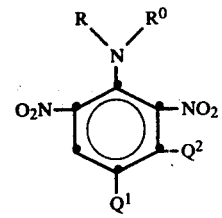

| $Q^1$ | $Q^2$ | R | $R^0$ |
|---|---|---|---|
| $CF_3$ | H | H | n-$C_3H_7$ |
| $CF_3$ | H | H | $CH(CH_3)CH(CH_3)C_2H_5$ |
| $CF_3$ | H | H | $CH(CH_3)CH_2CH(CH_3)C_2H_5$ |
| $CF_3$ | H | H | $CH(CH_3)CH_2CH_2CH(CH_3)_2$ |
| $CF_3$ | H | H | n-$C_5H_{11}$ |
| $CF_3$ | H | H | n-$C_6H_{13}$ |
| $CF_3$ | H | H | $CH_2CH(CH_3)_2$ |
| $CF_3$ | H | H | $CH(CH_3)C_2H_5$ |
| $CF_3$ | H | H | $CH(CH_3)C_5H_{11}$ |
| $CF_3$ | H | H | $CH(CH_3)C_4H_9$ |
| $CF_3$ | H | H | $CH(CH_3)C_3H_7$ |
| $CF_3$ | H | H | $CH(C_2H_5)_2$ |
| $CF_3$ | H | H | $CH(CH_3)CH(CH_3)_2$ |
| $CF_3$ | H | H | $N(C_3H_7)_2$ |
| $CF_3$ | H | $C_2H_5$ | $CH_2CH_2CHClCH_3$ |
| $CF_3$ | H | H | $CH\text{—}CH(CH_3)_2$ $\vert$ $CH(CH_3)_2$ |
| $CF_3$ | H | H | $CH(CH_3)CH_2OH$ |
| $CF_3$ | H | H | $CH_2\text{—}C\text{=}CH_2$ $\vert$ $CH_3$ |
| $CF_3$ | H | H | $N(C_2H_5)_2$ |
| $CF_3$ | H | H | ![piperidine ring]—N—$C_2H_5$ |
| $CF_3$ | H | H | $CH_3$ / —N \ $CH_3$ (2,6-dimethylpiperidino) |
| $CF_3$ | H | H | —N (with $C_2H_5$) |
| $CF_3$ | H | n-$C_3H_7$ | n-$C_3H_7$ |
| $CF_3$ | H | n-$C_3H_7$ | $C_2H_4Cl$ |
| $CF_3$ | H | n-$C_3H_7$ | cyclopropylmethyl |
| $CF_3$ | H | $C_2H_5$ | methallyl |
| $CF_3$ | Cl | $CH_3$ | $CH_3$ |
| $CF_3$ | Cl | H | $CH_3$ |
| $CF_3$ | Cl | H | $CH(CH_3)C_2H_5$ |
| $CF_3$ | Cl | $C_2H_5$ | n-$C_3H_7$ |
| $CF_3$ | Cl | n-$C_3H_7$ | methallyl |
| $CF_3$ | Cl | n-$C_3H_7$ | allyl |
| $CF_3$ | Cl | $C_2H_5$ | methallyl |
| $CF_3$ | Cl | n-$C_3H_7$ | n-$C_3H_7$ |
| $CF_3$ | Cl | H | $N(CH_3)_2$ |
| $CF_3$ | $N_3$ | $C_2H_5$ | $C_2H_5$ |
| $CF_3$ | $N_3$ | $CH_3$ | n-$C_3H_7$ |

-continued

| Q¹ | Q² | R | R⁰ |
|---|---|---|---|
| CF₃ | N₃ | H | CH(CH₃)C₂H₅ |
| CF₃ | N₃ | H | CH—CH(CH₃)₂<br>    \|<br>    CH(CH₃)₂ |
| CF₃ | N₃ | H | CH₃ |
| CF₃ | N₃ | H | CH(C₂H₅)₂ |
| CF₃ | N₃ | H | CH(C₂H₅)C₃H₇ |
| CF₃ | N₃ | CH₃ | CH₃ |
| CF₃ | N₃ | C₂H₅ | n-C₄H₉ |
| CF₃ | N₃ | C₂H₅ | n-C₃H₇ |
| CF₃ | N₃ | C₂H₅ | methallyl |
| CF₃ | N₃ | n-C₃H₇ | n-C₃H₇ |
| CF₃ | N₃ | H | N(CH₃)₂ |
| CF₃ | N₃ | H | CH(CH₃)CONHCH₃ |
| SO₂NHCH₂—N(CH₃)—(CH₃) ring | H | n-C₃H₇ | n-C₃H₇ |
| SO₂N=S(CH₃)₂ | H | n-C₃H₇ | n-C₃H₇ |
| SO₂NH₂ | H | n-C₃H₇ | n-C₃H₇ |
| SO₂CH₃ | H | n-C₃H₇ | n-C₃H₇ |
| SO₂N=CHN(CH₃)₂ | H | n-C₃H₇ | n-C₃H₇ |
| SO₂NHCH₂N(piperidine) | H | n-C₃H₇ | n-C₃H₇ |
| SO₂N=C(COCH₃)(CH₃) | H | n-C₃H₇ | n-C₃H₇ |
| SO₂N=CHOC₂H₅ | H | n-C₃H₇ | n-C₃H₇ |
| SO₂NHCH₂N(morpholine) | H | n-C₃H₇ | n-C₃H₇ |
| H | Cl | C₂H₅ | C₂H₅ |
| H | NH₂ | C₂H₅ | C₂H₅ |
| H | OCH₃ | C₂H₅ | C₂H₅ |
| CH₃ | Cl | CH₂CH(CH₃)₂ | methallyl |
| CH₃ | Cl | n-C₄H₉ | methallyl |
| CH₃ | Cl | H | CH(CH₃)CONHCH₃ |
| CH₃ | CH₃ | H | CH(C₂H₅)₂ |
| H | CH₃ | n-C₃H₇ | n-C₃H₇ |
| CH(CH₃)₂ | H | n-C₃H₇ | n-C₃H₇ |
| C(CH₃)₃ | H | H | CH(CH₃)C₂H₅ |
| CF₃ | OCH₃ | H | CH(C₂H₅)₂ |
| CF₃ | OCH₃ | n-C₃H₇ | n-C₃H₇ |
| CF₃ | OCH₃ | C₂H₅ | C₂H₅ |
| CF₃ | OH | C₂H₅ | C₂H₅ |
| CF₃ | OCH₃ | H | CH₃ |
| CF₃ | CH₃ | n-C₃H₇ | n-C₃H₇ |
| CF₃ | CO₂H | n-C₃H₇ | n-C₃H₇ |
| CF₃ | CONH₂ | H | CH(C₂H₅)₂ |
| CF₃ | CN | n-C₃H₇ | n-C₃H₇ |
| CF₃ | CONH₂ | C₂H₅ | n-C₄H₉ |
| CF₃ | OCH₃ | CH₃ | CH₃ |
| CF₃ | SCH₃ | H | CH(C₂H₅)₂ |
| CF₃ | SCN | H | CH(C₂H₅)₂ |
| CF₃ | SCH₂CO₂CH₃ | H | CH(C₂H₅)₂ |
| CF₃ | SCH₂CH₂CN | H | CH₃ |
| CF₃ | SCH₂CN | C₂H₅ | C₂H₅ |
| CF₃ | SCN | H | CH₃ |
| CF₃ | SCH₂CH₂CN | H | CH(C₂H₅)₂ |
| CF₃ | SCN | CH₃ | CH₃ |
| CF₃ | SCN | H | N(CH₃)₂ |
| CF₃ | SCN | n-C₃H₇ | n-C₃H₇ |
| CF₃ | SCN | C₂H₅ | C₂H₅ |
| CF₃ | NHCH₃ | H | CH₃ |
| CF₃ | NHCN | H | CH(C₂H₅)₂ |
| CF₃ | NHCN | n-C₃H₇ | n-C₃H₇ |
| CF₃ | NH₂ | H | CH(C₂H₅)₂ |
| CF₃ | NH₂ | n-C₃H₇ | n-C₃H₇ |
| CF₃ | NH₂ | C₂H₅ | C₂H₅ |
| CF₃ | NH₂ | C₂H₅ | methallyl |
| CF₃ | NH₂ | CH₃ | CH₃ |
| CF₃ | NH₂ | H | CH₃ |
| CF₃ | NH₂ | H | N(CH₃)₂ |
| CF₃ | NH₂ | H | CH(C₂H₅)C₃H₇ |
| CF₃ | HN₂ | H | CH(CH₃)C₃H₇ |

-continued

| $Q^1$ | $Q^2$ | R | $R^0$ |
|---|---|---|---|
| $CF_3$ | H | H | $N(CH_3)_2$ |
| $CF_3$ | H | H |  |
| $CF_3$ | NHCN | H | $n\text{-}C_3H_7$ |
| $SO_2N_3$ | H | $n\text{-}C_3H_7$ | $n\text{-}C_3H_7$ |
| $SO_2N(CH_3)OCH_3$ | H | $n\text{-}C_3H_7$ | $n\text{-}C_3H_7$ |
| $SO_2NH_2$ | H | $CH_3$ | $C_2H_5$ |
| $SO_2NH_2$ | H | H | $CH(C_2H_5)_2$ |
| $SO_2NHNH_2$ | H | $n\text{-}C_3H_7$ | $n\text{-}C_3H_7$ |
| $SO_2N(CH_3)_2$ | H | $n\text{-}C_3H_7$ | $n\text{-}C_3H_7$ |
| $SO_2NHCH_3$ | H | $n\text{-}C_3H_7$ | $n\text{-}C_3H_7$ |
| $SO_2NH_2$ | H | $C_2H_5$ | $C_2H_5$ |
| $SO_2N(CH_3)OH$ | H | $n\text{-}C_3H_7$ | $n\text{-}C_3H_7$ |
| $SO_2NHOCH_3$ | H | $n\text{-}C_3H_7$ | $n\text{-}C_3H_7$ |
| $SO_2NH_2$ | H | $C_2H_5$ | methallyl |
| $SO_2NH_2$ | H | $C_2H_5$ | $\underset{Cl}{CH_2C}=CH_2$ |
| $CF_3$ | $NHCOCH_3$ | $C_2H_5$ | $C_2H_5$ |
| $CF_3$ | Cl | H | $n\text{-}C_3H_7$ |
| $CF_3$ | Cl | $CH_3$ | $C_2H_5$ |
| $CF_3$ | SCN | $C_2H_5$ | $C_2H_5$ |
| $CF_3$ | NHCN | $C_2H_5$ | $C_2H_5$ |
| $CF_3$ | H | $CH_2CH_2Cl$ | $CH_2CH_2Cl$ |
| $CF_3$ | H | $C_2H_5$ | $CH_2CH_2OH$ |
| $CF_3$ | H | $C_2H_5$ | $\underset{Cl}{CH_2C}=CH_2$ |
| $CF_3$ | H | $n\text{-}C_3H_7$ | $CH_2CH=CH_2$ |
| $CF_3$ | H | $n\text{-}C_3H_7$ | $CH_2\underset{O}{\overset{\diagdown\diagup}{CH}}CH_2$ |
|  | H | $n\text{-}C_3H_7$ | $n\text{-}C_3H_7$ |
|  | H | $n\text{-}C_3H_7$ | $n\text{-}C_3H_7$ |
|  | H | $n\text{-}C_3H_7$ | $n\text{-}C_3H_7$ |
| 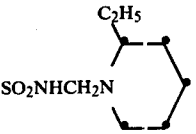 | H | $n\text{-}C_3H_7$ | $n\text{-}C_3H_7$ |
| 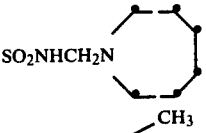 | H | $n\text{-}C_3H_7$ | $n\text{-}C_3H_7$ |
| 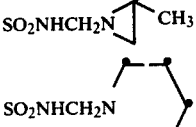 | H | $n\text{-}C_3H_7$ | $n\text{-}C_3H_7$ |
| 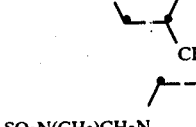 | H | $n\text{-}C_3H_7$ | $n\text{-}C_3H_7$ |
| 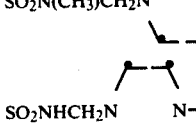 | H | $n\text{-}C_3H_7$ | $n\text{-}C_3H_7$ |
| $SO_2NH_2$ | H | $CH_2CH=CH_2$ | $CH_2CH=CH_2$ |
| $SO_2N_3$ | H | $CH_2CH=CH_2$ | $CH_2CH=CH_2$ |
| $SO_2NHOCH_3$ | H | $CH_2CH=CH_2$ | $CH_2CH=CH_2$ |

-continued

| $Q^1$ | $Q^2$ | R | $R^0$ |
|---|---|---|---|
| $SO_2N=S(C_2H_5)_2$ | H | $n-C_3H_7$ | $n-C_3H_7$ |
| $SO_2N=S(CH_3)C_2H_5$ | H | $n-C_3H_7$ | $n-C_3H_7$ |
| $SO_2NHSC_6H_5$ | H | $n-C_3H_7$ | $n-C_3H_7$ |
| $SO_2N=S(CH_3)C_6H_5$ | H | $n-C_3H_7$ | $n-C_3H_7$ |
| $SO_2N=S(C_6H_5)_2$ | H | $n-C_3H_7$ | $n-C_3H_7$ |
| $SO_2N=S(CH_2C_6H_5)_2$ | H | $n-C_3H_7$ | $n-C_3H_7$ |
| $CF_3$ | SCN | $CH_3$ | 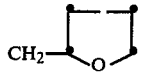 |
| $C(CH_3)_2CN$ | H | $C_2H_5$ | $C_2H_5$ |
| $SO_2N=C(C_2H_5)OC_2H_5$ | H | $n-C_3H_7$ | $n-C_3H_7$ |
| $SO_2N=C(C_6H_5)OCH_3$ | H | $n-C_3H_7$ | $n-C_3H_7$ |
| $CF_3$ | H | $CH_2CH=CH_2$ | $CH_2CH=CH_2$ |
| $CF_3$ | H | $CH_2CH_2CN$ | $CH_2CH_2CN$ |
| $CH_3$ | H | $CH_2CH_2Cl$ | $CH_2CH_2Cl$ |
| $CH_3$ | H | $CH_2CH_2OH$ | $CH_2CH_2OH$ |
| $CF_3$ | H | $n-C_3H_7$ | $CH_2CH_2OH$ |
| $C(CH_3)_2CN$ | H | H | $CH(CH_3)C_2H_5$ |
| $CF_3$ | SCN | $CH_3$ | $CH_2C\equiv CH$ |
| $C(CH_3)_3$ | H | $n-C_3H_7$ | $CH_2C=CH_2$ <br> $\|$ <br> $Cl$ |
| $CH_2CN$ | H | $n-C_3H_7$ | $n-C_3H_7$ |
| $SO_3CH_3$ | H | $n-C_3H_7$ | $n-C_3H_7$ |
| $SO_2NH_2$ | H | $n-C_3H_7$ | cyclopropylmethyl |
| $SO_2NH_2$ | H | $CH_3$ | $CH(CH_3)C_3H_7$ |
| $SO_2NH_2$ | H | $CH_2CH=CH_2$ | $CH_2C=CH_2$ <br> $\|$ <br> $CH_3$ |
| $SO_2NH_2$ | H | $n-C_3H_7$ | $CH_2CH(CH_3)_2$ |
| $SO_2Cl$ | H | $n-C_3H_7$ | $n-C_3H_7$ |
| $CF_3$ | NHCN | $CH_3$ | $CH_2C\equiv CH$ |
| $CF_3$ | NHCN | $CH_3$ | 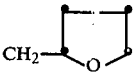 |
| $CF_3$ | NHCN | $n-C_3H_7$ | $CH_2C=CH_2$ <br> $\|$ <br> $Cl$ |
| $SO_2N(CH_3)SCCl_3$ | H | $n-C_3H_7$ | $n-C_3H_7$ |
| $SO_2N=C(CH_3)OC_4H_9$ | H | $n-C_3H_7$ | $n-C_3H_7$ |
| $SO_2N=C(C_6H_5)OC_2H_5$ | H | $n-C_3H_7$ | $n-C_3H_7$ |
| $SO_2NHOC_4H_9$ | H | $n-C_3H_7$ | $n-C_3H_7$ |
| $SO_2N=C(C_2H_5)OCH_3$ | H | $n-C_3H_7$ | $n-C_3H_7$ |
| $SO_2NH_2$ | H | $CH_3$ | cyclopentyl |
| $SO_2NHCH_3$ | H | $n-C_3H_7$ | cyclopropylmethyl |
| $Cl$ | H | $n-C_3H_7$ | $n-C_3H_7$ |
| $SO_2NHOH$ | H | $n-C_3H_7$ | $n-C_3H_7$ |

In general, the compounds used in this invention are prepared by methods now known to agricultural chemists.

Exceptions to this general rule are the 3-azido compounds of Formula II, the cyanamines of Formula III and some of the sulfur-containing compounds of Formula VIII, all of which are recently synthesized compounds.

Those compounds useful in this invention which are known in the herbicide art are prepared by methods described in the various patents listed in the prior art section of this specification and all of which are incorporated herein by reference. Since the preparative procedures described in such patents are sufficient to allow those skilled in the art to prepare the compounds, no attempt will be made here to further describe the preparation of such compounds.

The 3-azido compounds of Formula II, the cyanamines of Formula III and the sulfur-containing compounds of Formula VIII are prepared from the corresponding 3-chloro compounds. The 3-chloro compounds are intermediates in the preparation of the 1,3-phenylenediamines of U.S. Pat. No. 3,617,252 and the 3-alkoxy and alkylthio compounds of U.S. Pat. No. 3,764,624 and the preparation of the 3-chloro intermediates is described in both such patents.

The 3-azido compounds are prepared, for example, by the reaction of the corresponding 3-chloro compound with an alkali metal azide such as sodium azide in the presence of an inert solvent such as dimethylformamide. The reaction is conveniently run at room temperature. The 3-thiocyanato compounds are prepared in a similar manner employing an alkali metal sulfide such as sodium sulfide and cyanogen chloride. Compounds bearing a cyanomethylthio group in the 3-position are prepared from the corresponding 3-chloro compound by reaction with sodium sulfide and chloroacetonitrile. The other sulfur-containing compounds are prepared by reaction of the 3-chloro compound with the appropriate mercapto compound in the presence of an alkali metal hydroxide such as lithium hydroxide or potassium hydroxide. The cyanamines are prepared by heating the 3-chloro intermediate with cyanamide in the presence of a tertiary amine such as triethylamine.

While it is believed that those skilled in the art can prepare all the compounds useful in the present invention, the following preparative examples are given to insure that the novel compounds described above can be readily prepared.

EXAMPLE 1

A solution of 2.3 g. of sodium azide in 15 ml. of water was added dropwise to a solution of 7 g. of 3-chloro-N,N-dimethyl-2,6-dinitro-4-trifluoromethylaniline in 90 ml. of dimethylformamide at room temperature. The mixture was stirred at room temperature for one hour, poured over ice-water and filtered to recover 6.9 g. (94%) of 3-azido-N,N-dimethyl-2,6-dinitro-4-trifluoromethylaniline, m.p. 66°–67° C. The structure was confirmed by the NMR and IR spectra and elemental analysis.

Calculated: C, 33.76; H, 2.20; N, 26.25. Found: C, 33.98; H, 2.19; N, 26.53.

EXAMPLE 2

A solution of 0.75 g. of sodium azide in 15 ml. of water was added dropwise to a solution of N-n-butyl-3-chloro-2,6-dinitro-N-ethyl-4-trifluoromethylaniline in 75 ml. of dimethylformamide at room temperature. The mixture was stirred at room temperature for 2 hours and poured over ice-water. The product separated as an oil. The mixture was extracted three times with methylene chloride, the methylene chloride was evaporated, the residue taken up in ether, and the ether solution extracted three times with water. Evaporation of the ether left 3.1 g. (92%) of 3-azido-N-n-butyl-2,6-dinitro-N-ethyl-4-trifluoromethylaniline as an oil. The structure was confirmed by the NMR and IR spectra and elemental analysis.

Calculated: C, 41.49; H, 4.02; N, 22.33. Found: C, 41.39; H, 3.89; N, 22.10.

EXAMPLE 3

A solution of 1.0 g. of sodium azide in 10 ml. of water was added dropwise to a solution of 3.2 g. of N-(3-chloro-2,6-dinitro-4-trifluoromethylphenyl)-N',N'-dimethylhydrazine in 80 ml. of dimethylformamide at room temperature. The mixture was stirred at room temperature for one hour, poured over ice-water and filtered. The solid product was dried and recrystallized from 2B ethanol to yield 3.1 g. (93%) of N-(3-azido-2,6-dinitro-4-trifluoromethylphenyl)-N',N'-dimethylhydrazine, m.p. 123°–125° C. The structure was confirmed by the NMR and IR spectra and elemental analysis.

Calculated: C, 32.25; H, 2.41; N, 29.25. Found: C, 32.21; H, 2.39; N, 29.34.

Following the procedure of Example 1, 2 or 3, the following additional compounds of Formula II were prepared.

| $R^4$ | $R^5$ | Melting Point, °C. |
|---|---|---|
| $C_2H_5$ | $C_2H_5$ | Oil |
| H | $CH(CH_3)C_3H_7$ | Oil |
| H | $CH(CH_3)C_2H_5$ | 77–78 |
| H | $CH[CH(CH_3)_2]_2$ | Oil |
| H | $CH(C_2H_5)C_3H_7$ | 27–28 |
| H | $CH_3$ | 118–120 |
| $C_2H_5$ | $n-C_3H_7$ | Oil |
| H | $CH(C_2H_5)_2$ | 77–79 |
| $n-C_3H_7$ | $n-C_3H_7$ | Oil |
| H | $CH(CH_3)CONHCH_3$ | 163, dec. |
| H | $n-C_3H_7$ | 70–72 |
| $C_2H_5$ | methallyl | 46–48 |

EXAMPLE 4

A solution of 40 g. of 3-chloro-2,6-dinitro-N-(3-pentyl)-4-trifluoromethylaniline, 10.5 g. of cyanamide and 30 g. of triethylamine in 250 ml. of 3A ethanol was heated under reflux for 5 days. The solution was allowed to cool and was then poured over ice-water. The product which separated was recrystallized from 3A ethanol-water to give 36 g. (71%) of 3-cyanamino-2,6-dinitro-N-(3-pentyl)-4-trifluoromethylaniline, triethylamine salt, m.p. 135°–137° C. The structure was confirmed by the NMR and IR spectra and elemental analysis.

Calculated: C, 49.35; H, 6.32; N, 18.17. Found: C, 49.56; H, 6.06; N, 18.37.

Following the procedure of Example 4, the following additional compounds of Formula III were prepared. All were obtained as the triethylamine salt.

| $R^7$ | $R^8$ | $R^9$ | Melting Point, °C. |
|---|---|---|---|
| CN | $n-C_3H_7$ | $n-C_3H_7$ | 102–103 |
| CN | $C_2H_5$ | $C_2H_5$ | 122–124 |
| CN | H | $n-C_3H_7$ | 130–131 |
| CN | $CH_3$ | $C_2H_5$ | 84–86 |
| CN | $CH_3$ | tetrahydrofurfuryl ($CH_2$–O ring) | 98–100 |
| CN | $CH_3$ | $CH_2C{\equiv}CH$ | 129–132 |
| CN | $n-C_3H_7$ | $CH_2C(Cl){=}CH_2$ | 68–70 |

The following cyanamino free bases were prepared by neutralizing the corresponding triethylamine salts with dilute hydrochloric acid in diethyl ether at room temperature.

| $R^7$ | $R^8$ | $R^9$ | Melting Point, °C. |
|---|---|---|---|
| CN | $C_2H_5$ | $C_2H_5$ | 195–198 |
| CN | H | $CH(C_2H_5)_2$ | 106–110 |
| CN | H | $n-C_3H_7$ | 140–143 |

EXAMPLE 5

To a cold solution of 40 g. of 3-chloro-2,6-dinitro-N-(3-pentyl)-4-trifluoromethylaniline in 400 ml. of dimethylformamide was added 36 g. of sodium sulfide nonahydrate in 100 ml. of water. The mixture was stirred for one-half hour and cyanogen chloride was bubbled into the cold solution for 10 minutes. The dark solution became light red. The reaction mixture was poured over ice-water and the solid product separated. Recrystallization from 3A ethanol-water gave 39 g. (89%) of 2,6-dinitro-N-(3-pentyl)-3-thiocyanato-4-trifluoromethylaniline, m.p. 97°–99° C. The structure was confirmed by the NMR spectrum and elemental analysis.

Calculated: C, 41.27; H, 3.46; N, 14.81. Found: C, 41.02; H, 3.40; N, 14.56.

Following the procedure of Example 5, the following additional compounds of Formula VIII were prepared.

| Q | $R^{23}$ | $R^{24}$ | Melting Point, °C. |
|---|---|---|---|
| SCN | H | $CH_3$ | 125–126 |
| SCN | $CH_3$ | $CH_3$ | 153–155 |
| SCN | H | $N(CH_3)_2$ | 146–148 |
| SCN | $n-C_3H_7$ | $n-C_3H_7$ | Oil |

-continued

| Q | $R^{23}$ | $R^{24}$ | Melting Point, °C. |
|---|---|---|---|
| SCN | $C_2H_5$ | $C_2H_5$ | 116–118 |
| SCN | $CH_3$ | $CH_2\text{-}O\text{-}CH_2$ (oxetane) | 75–76 |
| SCN | $CH_3$ | $CH_2C\equiv CH$ | 84–86 |
| SCN | $C_2H_5$ | $CH_2C(CH_3)=CH_2$ | 92–94 |

The preparation of 3-cyanomethylthio compounds is illustrated by the following example.

EXAMPLE 6

A mixture of 3.4 g. of 3-chloro-N,N-diethyl-2,6-dinitro-4-trifluoromethylaniline and 2.4 g. of sodium sulfide nonahydrate in dimethyl sulfoxide was stirred for one hour at 0° C. Chloroacetonitrile (0.76 g.) was added and the mixture was stirred overnight at room temperature. The reaction mixture was poured over ice and extracted with either. The ether was evaporated and the residue was recrystallized twice from ethanol to yield 2.7 g. of 3-cyanomethylthio-N,N-diethyl-2,6-dinitro-4-trifluoromethylaniline, m.p. 77°–79° C. The structure was confirmed by the NMR spectrum.

The dinitroanilines of this invention have been shown to be effective in reducing the vigor of soil-borne phytophthora phytopathogens in in vivo tests. The tests reported below are exemplary of the compounds' potency.

These tests were performed by growing soybean seedlings in the greenhouse in soil heavily infested with *Phytophthora megasperma var. sojae*. The soil was obtained from a field where phytophthora-infected soybeans had been grown, and was further inoculated by mixing into the soil chopped soybean plants infected with *P. megasperma*.

The test compounds were formulated by dissolving them in a minimum amount of ethanol, and dispersing the ethanol solution in about 25 ml. of water which was mixed into approximately 10 kg. of screened phytophthora-infested soil. The soil was then spread into metal greenhouse flats, and Corsoy soybean seeds were planted.

Application rates of the test compounds were measured in kilograms per hectare of soil surface, and a sufficient quantity of each test compound was used to supply the application rates named in the tables below.

The flats were stored in the greenhouse and watered regularly for about 4 weeks, at which time the disease control effected by the test compounds was observed. The control was reported as percent control, compared to infested, untreated control plants.

Table 1

| Compound | Appln. Rate kg./ha. | Percent Control |
|---|---|---|
| 3,5-dinitro-$N^4,N^4$-di(n-propyl)-$N^1$-(2,5-dimethyl-pyrrolidinomethyl)-sulfanilamide | 0.28 | 62 |
|  | 0.56 | 72 |
|  | 1.1 | 90 |
|  | 2.2 | 89 |
|  | 4.5 | 100 |
| 3,5-dinitro-$N^4,N^4$-di(n-propyl)-$N^1$-hexahydroazepino-methylsulfanil-amide | 0.28 | 27 |
|  | 0.56 | 28 |
|  | 1.1 | 55 |
|  | 2.2 | 100 |
|  | 4.5 | 100 |
| 3,5-dinitro-$N^4,N^4$-di(n-propyl)-$N^1$-(1-methoxyethylidene)sulfanilamide | 0.28 | 12 |
|  | 0.56 | 0 |
|  | 1.1 | 84 |
|  | 2.2 | 100 |
|  | 4.5 | 100 |
| 3,5-dinitro-$N^4$-ethyl-$N^4$-propyl-sulfanilamide | 0.56 | 34 |
|  | 1.1 | 34 |
|  | 2.2 | 80 |
| $N^4$-(2-chloroallyl)-$N^4$-ethyl-3,5-dinitro-sulfanilamide | 0.56 | 50 |
|  | 1.1 | 63 |
|  | 2.2 | 80 |
| 3,5-dinitro-$N^4,N^4$-di(n-propyl)-$N^1$-methyl-$N^1$-trichloromethylthiosulfanilamide | 1.1 | 42 |
|  | 2.2 | 62 |
|  | 4.5 | 62 |
| 2,6-dinitro-N-(2-hydroxyethyl)-N-(n-propyl)-4-trifluoromethyl-aniline | 1.1 | 67 |
|  | 2.2 | 13 |
|  | 4.5 | 80 |
| $N^4$-cyclopentyl-3,5-dinitro-$N^4$-methylsulfanilamide | 1.1 | 80 |
|  | 2.2 | 70 |
|  | 4.5 | 61 |
| 3-cyanamino-2,6-dinitro-N-(3-pentyl)-4-trifluoromethylaniline, triethylamine salt | 1.1 | 70 |
|  | 2.2 | 62 |
|  | 4.5 | 15 |
| 2,6-dinitro-N-(3-pentyl)-3-thiocyanato-4-trifluoromethylaniline | 1.1 | 63 |
|  | 2.2 | 81 |
|  | 4.5 | 63 |
| 2,6-dinitro-$N^1,N^1$-diethyl-4-trifluoromethyl-1,3-phenylenediamine | 0.56 | 55 |
|  | 1.1 | 52 |
|  | 2.2 | 84 |
| 2,6-dinitro-N,N-di(n-propyl)-4-methylsulfonyl-aniline | 1.1 | 59 |
|  | 2.2 | 62 |
|  | 4.5 | 100 |
| 3,5-dinitro-$N^4,N^4$-di(n-propyl)sulfanilamide | 1.1 | 6 |
|  | 2.2 | 80 |
|  | 4.5 | 91 |
| 2,6-dinitro-N,N-di(n-propyl)-4-trifluoromethyl-aniline | 1.1 | 16 |
|  | 2.2 | 55 |
|  | 4.5 | 78 |
| $N^4,N^4$-diethyl-3,5-dinitro-sulfanilamide | 1.1 | 29 |
|  | 2.2 | 51 |
|  | 4.5 | 49 |
| 4-azidosulfonyl-3,5-dinitro-N,N-di(n-propyl)aniline | 1.1 | 35 |
|  | 2.2 | 86 |
|  | 4.5 | 100 |

The test data reported above show that the compounds of this invention are particularly useful for the protection of plants from the adverse effects of soil-borne phytophthora phytopathogens. Accordingly, the invention is a new method of reducing the adverse effects of soil-borne phytophthora phytopathogens which comprises applying to phytophthora-infested soil a fungicidally-effective amount of a compound described herein.

As agricultural chemists will understand, practice of the method does not necessarily kill all, or even any, of the phytopathogens. As the data above show, application of a fungicidally-effective amount of a compound reduces the adverse effects of the disease, even though only a part, or even none, of the phytopathogen population may be killed by the compound. The term "fungicidally-effective amount" is used here to describe an amount which is sufficient to reduce the adverse effects of a soil-borne phytophthora phytopathogen. The term "reducing the adverse effects" refers to weakening the pathogen sufficiently that its reproduction rate and its vigor are decreased, with the result that the express signs of the disease, and the concomitant injury to the host plant, are decreased as compared with phytopathogens affecting plants growing in untreated soil.

The method of this invention is widely useful against the various plant diseases which are caused by soil-borne phytophthora phytopathogens. The following phytophthora organisms and diseases caused thereby are typical and illustrative of the phytopathogens controlled by this invention, but are by no means exhaustive thereof.

*Phytophthora cactorum* and *P. parasitica,* causative of stem and crown rot of tomato, cucurbits, rhubarb, apple, pear, strawberry, eggplant and pea

*P. capsici,* causative of root and fruit rot of pepper

*P. cinnamoni,* causative of root rot of avocado

*P. fragariae,* causative of red stele of strawberry

*P. megasperma,* causative of root rot of crucifers

*P. palmivora,* causative of root rot of citrus fruit trees and rubber

*P. parasitica* var. *nicotianae,* causative of black shank of tobacco

The method is preferably used for protecting soybeans from *Phytophthora megasperma,* the causative phytopathogen of soybean root rot. The compounds with which the method is preferably carried out are 3,5-dinitro-$N^4,N^4$-di(n-propyl)-$N^1$-(2,5-dimethylpyrrolidinomethyl)sulfanilamide, 3,5-dinitro-$N^4,N^4$-di(n-propyl)-$N^1$-hexahydroazepinomethylsulfanilamide, 3,5-dinitro-$N^4,N^4$-di(n-propyl)-$N^1$-(1-methoxyethylidene)-sulfanilamide, 2,6-dinitro-N,N-di(n-propyl)-4-methylsulfonylaniline, 3,5-dinitro-$N^4,N^4$-di(n-propyl)sulfanilamide, and 4-azidosulfonyl-3,5-dinitro-N,N-di(n-propyl)aniline.

As is usual in the protection of plants from soil-borne phytopathogens, the method of this invention will be usually carried out by applying the compounds to the soil at approximately the same time that the crop is being planted, as by incorporating the compound in the soil as the seed bed is being prepared. The method may also be used to benefit established plants by applying a compound of the invention to the soil around such plants.

The methods of formulating the compounds and preparing dispersions of the formulations, and the methods of applying dispersions of the compounds to the soil, are entirely conventional in the plant protection art. Some explanation of the methods of application will be given merely to assure that those skilled in the art can readily carry out the invention.

It is most meaningful to describe the application rate in terms of the amount of compound applied per unit area of soil. Compound application rates in the range of from about 0.1 to about 10 kg./ha. are used in the practice of this invention. Application rates higher and lower than the named range will at times be useful, depending upon the severity of the phytopathogenic infection, the weather, which has a strong effect on the vigor of phytopathogens, and the characteristics of the specific compound in use. Preferred application rates are in the general range of from about 0.5 to about 5 kg./ha.

The dispersions in which the compounds are applied are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usally from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

The compounds can economically and conveniently be applied to the soil in the form of granular formulations. Such formulations, well known to the agricultural chemical art, are prepared by dispersing the compound on an inert carrier of controlled granular character. Most often, the carrier is a coarsely ground clay, such as attapulgite or kaolin clay, having a particle size in the range of from 0.5 to 3 mm. Such granular formulations are easily applied to the soil with applicators which are specially designed to apply accurately controlled amounts of the granular products to the soil.

I claim:

1. A method of reducing the adverse effects of soil-borne phytophthora pathogens which comprises applying to soil infested with such phytopathogens a fungicidally-effective amount of an active agent selected from the group consisting of 2,6-dinitro-N,N-di(n-propyl)-4-trifluoromethylaniline;

2,6-dinitro-$N^1,N^1$-diethyl-4-trifluoromethyl-1,3-phenylenediamine;

2,6-dinitro-N,N-di(n-propyl)-4-methylsulfonylaniline;
and the five compounds of the formula

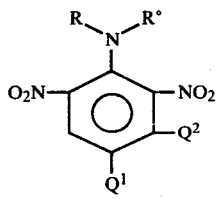

(1) wherein $Q^1=CF_3$, $Q^2=H$, $R=C_2H_5$, and $R°=$methallyl;
(2) wherein $Q^1=SO_2N=S(CH_3)_2$, $Q^2=H$, $R=n—C_3H_7$, and $R°=n—C_3H_7$;
(3) wherein $Q^1=CF_3$, $Q^2=H$, $R=n—C_3H_7$, and $R°=C_2H_4Cl$;
(4) wherein $Q^1=CH_3$, $Q^2=H$, $R=CH_2CH_2Cl$, and $R°=CH_2CH_2Cl$;
(5) wherein $Q^1=CF_3$, $Q^2=NH_2$, $R=n—C_3H_7$, and $R°=n—C_3H_7$.

2. The method of claim 1 wherein the active agent is the compound of the formula

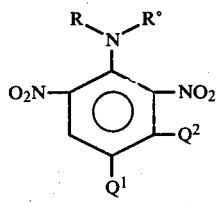

wherein $Q^1=CF_3$, $Q^2=H$, $R=C_2H_5$, and $R°=$methallyl.

3. The method of claim 1 wherein the active agent is the compound of the formula

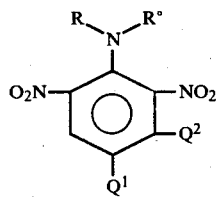

wherein $Q^1=SO_2N=S(CH_3)_2$, $Q^2=H$, $R=n—C_3H_7$, and $R°=n—C_3H_7$.

4. The method of claim 1 wherein the active agent is the compound of the formula

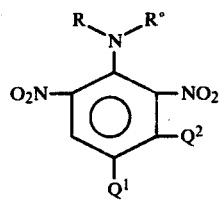

wherein $Q^1=CF_3$, $Q^2=H$, $R=n—C_3H_7$, and $R°=C_2H_4Cl$.

5. The method of claim 1 wherein the active agent is the compound of the formula

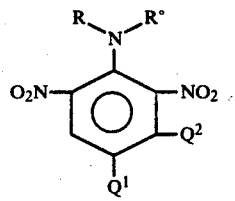

wherein $Q^1=CH_3$, $Q^2=H$, $R=CH_2CH_2Cl$, and the $R°=CH_2CH_2Cl$.

6. The method of claim 1 wherein the active agent is the compound of the formula

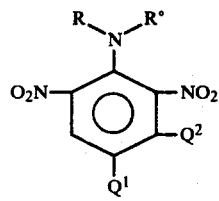

wherein $Q^1=CF_3$, $Q^2=NH_2$, $R=n—C_3H_7$, and $R°=n—C_3H_7$.

7. The method of claim 1 wherein the active agent is 2,6-dinitro-N,N-di(n-propyl)-4-trifluoromethylaniline.

8. The method of claim 1 wherein the active agent is 2,6-dinitro-$N^1,N^1$-diethyl-4-trifluoromethyl-1,3-phenylenediamine.

9. The method of claim 1 wherein the active agent is 2,6-dinitro-N,N-di(n-propyl)-4-methylsulfonylaniline.

10. The method of claim 1 wherein the soil-borne phytophthora pathogen is *Phytophthora megasperma*.

11. The method of claim 10 wherein the active agent is 2,6-dinitro-N,N-di(n-propyl)-4-trifluoromethylaniline.

* * * * *

Disclaimer 4,156,722.—*James D. Froyd*, Fountaintown, Ind. DINITROANILINES FOR CONTROL OF SOIL-BORNE PHYTOPATHOGENS. Patent dated May 29, 1979. Disclaimer filed Feb. 4, 1980, by the assignee, *Eli Lilly and Company*.

Hereby enters this disclaimer to claims 1–11, all the claims of said patent.

[*Official Gazette, April 1, 1980.*]